(12) United States Patent
Ghalib et al.

(10) Patent No.: US 9,878,123 B2
(45) Date of Patent: Jan. 30, 2018

(54) SURGICAL HUMIDIFIER CONTROL

(71) Applicant: Fisher & Paykel Healthcare Limited, Auckland (NZ)

(72) Inventors: Ali Ghalib Abdul Rahman Ghalib, Auckland (NZ); Lina Tessy, Auckland (NZ); Joseph Patrick Walter Strevens, Auckland (NZ); Paul David Phillips, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 996 days.

(21) Appl. No.: 14/023,391

(22) Filed: Sep. 10, 2013

(65) Prior Publication Data

US 2014/0116433 A1    May 1, 2014

Related U.S. Application Data

(60) Provisional application No. 61/699,773, filed on Sep. 11, 2012.

(51) Int. Cl.
*A61M 16/16* (2006.01)
*A61M 16/10* (2006.01)
A61M 16/00 (2006.01)

(52) U.S. Cl.
CPC ........ *A61M 16/16* (2013.01); *A61M 16/1075* (2013.01); *A61M 16/108* (2014.02); *A61M 16/109* (2014.02); *A61M 16/1085* (2014.02); *A61M 16/1095* (2014.02); *A61M 16/161* (2014.02); *A61M 2016/0039* (2013.01); *A61M 2205/3368* (2013.01)

(58) Field of Classification Search
CPC ................ A61M 16/16; A61M 16/161; A61M 16/1075; A61M 16/108; A61M 16/1085; A61M 2016/0039; A61M 2205/3368
See application file for complete search history.

(56) References Cited

U.S. PATENT DOCUMENTS

| 6,272,933 B1 * | 8/2001 | Gradon | A61M 16/1095 128/203.16 |
| 2004/0102731 A1 * | 5/2004 | Blackhurst | A61B 1/00154 604/26 |

FOREIGN PATENT DOCUMENTS

WO    WO 0113981 A1 *    3/2001    ............ A61M 16/16

* cited by examiner

*Primary Examiner* — Imani Hayman
*Assistant Examiner* — Nilay Shah
(74) *Attorney, Agent, or Firm* — Knobbe, Martens, Olson & Bear, LLP

(57) ABSTRACT

Some embodiments provide for humidifier control systems and methods configured to adjust power to a heater plate in a surgical humidifier to account for changes in flow rate to provide a consistent output, to provide functionality for different modes of use, and to provide accurate control over temperature and/or humidity at relatively low flows. The humidifier control system can receive a flow rate reading and determine a power requirement corresponding to the received flow rate reading, wherein the power requirement is one of a plurality of set points which correspond to ranges of flow rates. The humidifier control system can determine a mode of use based at least in part on the flow rate reading. The humidifier control system can provide electrical power to the heater plate according to the power requirement and/or the mode of use.

21 Claims, 10 Drawing Sheets

SURGICAL HUMIDIFIER CONTROL

CROSS-REFERENCE TO RELATED APPLICATIONS

This application claims the benefit of priority under 35 U.S.C. § 119(e) to U.S. Provisional Patent Application No. 61/699,773, entitled "SURGICAL HUMIDIFIER CONTROL," filed Sep. 11, 2012, which is incorporated herein by reference in its entirety.

BACKGROUND

Field

This disclosure relates generally to heating and humidifying gases, and more particularly to heating and humidifying insufflation gases for use in surgery.

Description of Related Art

Insufflation gases can be used in surgery for a variety of purposes. In open surgery, gas can be insufflated into a body cavity for de-airing, as in cardiac surgery. In laparoscopic surgery, the abdominal wall can be distended using gas to provide room for instrument insertion and tissue dissection. The insufflation gas can be inert or non-toxic, such as air or carbon dioxide ($CO_2$). Medical grade $CO_2$ can be supplied in cylinders and delivered to a patient at room temperature (e.g., between about 19 and 21 degrees Celsius), with a relative humidity approaching 0%. This gas is colder and drier than the environment inside the patient (e.g. about 37 degrees Celsius and a relative humidity of about 100%, respectively). Temperature and humidity of an insufflation gas can be adjusted to more closely approximate the environment inside the patient prior to delivery. Heating and humidifying the insufflation gas can decrease cellular damage or desiccation, limit adhesion formation, or reduce other deleterious effects.

SUMMARY

The systems, methods and devices described herein have innovative aspects, no single one of which is indispensable or solely responsible for their desirable attributes. Without limiting the scope of the claims, some of the advantageous features will now be summarized.

According to some embodiments, a method is provided that allows the humidifier to adjust power to a heater plate to account for changes in flow rate to provide a consistent output. The method can include receiving a flow rate reading from a flow sensor configured to sense a flow rate of a gas exiting a chamber of the surgical humidifier. The method can include determining a power requirement corresponding to the received flow rate reading, wherein the power requirement is one of a plurality of set points which correspond to ranges of flow rates. The method can include providing electrical power to a heater plate in the surgical humidifier according to the power requirement.

According to some embodiments, a method is provided for use with a surgical humidifier that uses other sensors in addition to a chamber outlet sensor to control power to a heater plate at relatively low flows. The method can include receiving a flow rate reading from a flow sensor configured to sense a flow rate of a gas exiting a chamber of the surgical humidifier. The method can include selecting a low flow mode based on the flow rate reading wherein the low flow mode is selected when the received flow rate reading is less than a low flow threshold. The method can include providing electrical power to a heater plate in the surgical humidifier to achieve a defined temperature set point corresponding to the low flow mode.

According to some embodiments, a method is provided for use with a surgical humidifier that allows the humidifier to be switched on and to stay warm and ready before gas flow starts. The method can include detecting a pre-heat mode. The method can include determining a heater plate temperature set point. The method can include receiving a heater plate temperature reading from a heater plate sensor. The method can include providing electrical power to a heater plate in the surgical humidifier to achieve the heater plate temperature set point.

According to some embodiments, a method is provided for use with a surgical humidifier that allows the humidifier to detect a mode of use, and to change the humidifier control algorithm accordingly. The method can include receiving a flow rate reading from a flow sensor configured to sense a flow rate of a gas exiting a chamber of the surgical humidifier. The method can include starting a timer when the flow rate reading exceeds a flow rate threshold. The method can include switching to a high flow mode when the flow rate exceeds the flow rate threshold for a defined duration. The method can include providing electrical power to a heater plate in the surgical humidifier to achieve a chamber outlet temperature set point corresponding to the high flow mode.

According to some embodiments, a surgical humidifier is provided wherein the humidifier is configured to respond to varying flow rates of a gas. The humidifier can include a humidifier body and a chamber configured to removably engage with the humidifier body and hold a volume of water. The chamber can include an inlet port configured to receive a gas from an inlet conduit and an outlet port configured to direct a humidified gas to a patient conduit. The humidifier can include a chamber outlet temperature sensor configured to measure a temperature of the humidified gas. The humidifier can include a flow sensor configured to measure a flow rate of the humidified gas. The humidifier can include a heater plate coupled to the humidifier body and configured to deliver heat to the chamber. The humidifier can include a humidifier control system electrically coupled to the heater plate, the humidifier control system being configured to control an amount of electrical power to the heater plate. The humidifier can be configured to receive a temperature measurement from the chamber outlet temperature sensor, to receive a flow rate reading from the flow sensor, to determine a chamber outlet temperature set point in response to the received flow rate reading, and to adjust the amount of electrical power to the heater plate based on a difference between the chamber outlet temperature set point and the temperature measurement.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
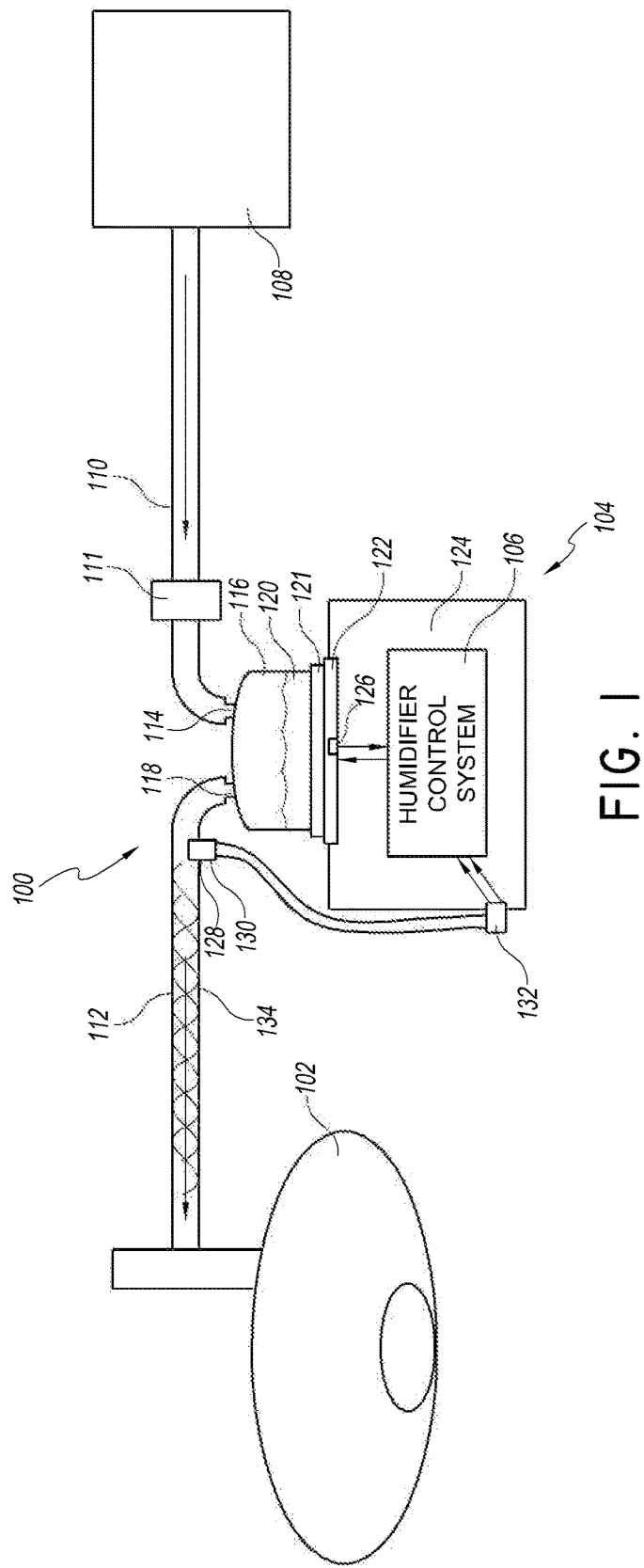
FIG. 1 illustrates an example surgical humidification system for delivering temperature-controlled and humidity-controlled gas to a patient, the surgical humidification system having a humidifier incorporating a humidifier control system.

Described herein are methods and systems that increase control, consistency, and/or efficiency of humidifiers across a range of flow rates and in a variety of usage scenarios. It will be understood that although much of the description herein is in the context of open or laparoscopic surgery, one or more features of the present disclosure can also be implemented in other scenarios where it is desirable to output a gas having a defined temperature and/or humidity, such as during minimally invasive procedures, endoscopic surgery, and respiratory applications.

Insufflation gases can be used in a variety of surgical procedures. In laparoscopic surgery, insufflation gases can be used to create a viewing space for a surgeon to operate and manipulate instruments within a patient. In open surgery, insufflation gases can be used in a body cavity for de-airing. These environments can include cells that are susceptible to damage when exposed to relatively dry and cold gases. For example, the peritoneum is a delicate single layer structure and may be damaged when exposed to climatic change. Insufflation gases can be relatively cold and dry and may cause damage to the peritoneum, damage that can be reduced or avoided through humidifying and warming the insufflation gas. Relatively large volumes of gas can be used in some laparoscopic operations (e.g., up to about 500 L in some cases). An effect of this continuous flow of cold, dry gas on the lining of the abdominal cavity can be significant, causing structural changes that may contribute to post-operative pain and scarring (e.g., adhesions).

It can be desirable to prevent damage that could lead to downstream problems. For example, cold, dry gas can cause evaporative cooling and desiccation inside a patient's peritoneum. Warming and humidifying the insufflation gas can reduce or prevent this desiccation and sequential cooling and cellular desiccation, which in turn can limit adhesion formation. This can have a positive effect on post-operative pain that not only increases quality of care but reduces recovery time and increase department throughput. Warming and humidifying insufflation gases may reduce intra-operative hypothermia, reduce post-operative pain, and improve post-operative recovery.

Some embodiments described herein provide for a humidification system that is configured to deliver warm, humidified gas to a patient undergoing a surgical procedure. The gas is passed through a water chamber which is filled with water that is heated using a heater plate. Water evaporates in the chamber and combines with the gas which flows over it, thereby heating and/or humidifying the gas. The temperature of the gas can be maintained as it travels along a heated tube to an outlet port for delivery to the patient. The humidification system can monitor the temperature and flow rate of the gas at a chamber outlet, and control an amount of electrical power delivered to the heater plate to provide a gas having a desired temperature and humidity. Thus, surgical gas from a gas source (e.g., an insufflator, a gas bottle, or the like) can be humidified and heated and delivered to the patient, enabling the patient's peritoneum or other targeted area to remain moist and warm.

Some embodiments described herein provide for a surgical humidification system that includes a humidifier control system configured to determine a mode of operation, a mode of control, a heater plate set point, or any combination of these. The humidifier control system can base this determination at least in part on feedback from components of the humidification system. The components of the humidification system can provide feedback through sensors or other electrical components, and feedback can include, for example, outlet gas temperature, heater plate temperature, heater plate power, gas flow rate, user input through user interface elements, duration of operation, and the like. Some embodiments of the humidifier control system can improve efficiency of the humidification system, provide an output gas with relatively consistent humidity and temperature, and provide greater control over temperature and humidity of the gas compared to control systems that do not incorporate system component feedback. The humidifier control system can provide at least some of these improvements through modules configured to process system component feedback and adjust output settings according to a control loop feedback mechanism.

Example Surgical Humidification System

FIG. 1 illustrates an example surgical humidification system 100 for delivering temperature- and humidity-controlled gas to a patient 102, the surgical humidification system 100 having a humidifier 104 incorporating a humidifier control system 106. The humidifier 104 is connected to a gas source 108 (e.g., an insufflator) through an inlet conduit 110. The humidifier 104 delivers humidified gas to the patient 102 through a patient conduit 112. The conduits 110, 112 can be made of flexible plastic tubing.

The humidifier 104 receives gas from the gas source 108 through the inlet conduit 110. The gas can be filtered through a filter 111 and delivered to the humidifier 104 through a humidifier inlet 114. The gas is humidified as it passes through a humidifying chamber 116, which is effectively a water bath, and the gas flows out through a humidifier outlet 118 and into the patient conduit 112. The gas then moves through the patient conduit 112 to the patient 102. In some embodiments, a filter can be disposed between the humidifier outlet 118 and the patient 102.

The humidifier 104 comprises a body 124 removably engageable with the humidification chamber 116. The humidification chamber 116 has a metal base 121 and is adapted to hold a volume of water 120, which can be heated by a heater plate 122. The heater plate 122 can be in thermal contact with the metal base 121 of the humidification chamber 116. Providing power to the heater plate 122 can cause heat to flow from the heater plate 122 to the water 120 through the metal base 121. As the water 120 within the humidification chamber 116 is heated it can evaporate and the evaporated water can mix with gases flowing through the humidification chamber 116 from the filter 111 and gas source 108. Accordingly, the humidified gases leave the humidification chamber 116 via outlet 118 and are passed to the patient via the patient conduit 112 and into the surgical site to, for example, insufflate and/or expand the surgical site or peritoneal cavity.

The humidifier 104 includes the humidifier control system 106 configured to control a temperature and/or humidity of the gas being delivered to the patient 102. The humidifier control system 106 can be configured to regulate an amount of humidity supplied to the gases by controlling an electrical power supplied to the heater base 122. The humidifier control system 106 can control operation of the humidification system 104 in accordance with instructions set in software and in response to system inputs. System inputs can include a heater plate sensor 126, an outlet chamber temperature sensor 128, and a chamber outlet flow sensor 130. For example, the humidifier control system 106 can receive temperature information from the heater plate sensor 126 which it can use as an input to a control module used to control the power or temperature set point of the heater plate 122. The humidifier control system 106 can be provided with inputs of temperature and/or flow rates of the gases. For example, the chamber outlet temperature sensor 128 can be provided to indicate to the humidifier control system 106 the temperature of the humidified gas as it leaves the outlet 118 of the humidification chamber 116. The temperature of the gases exiting the chamber can be measured using any suitable temperature sensor 128, such as a wire-based temperature sensor. The chamber outlet flow sensor 130 can be provided to indicate to the humidifier control system 106 the flow rate of the humidified gas. The flow rate of the gases through the chamber 116 can be measured using any suitable flow sensor 130, such as a hot wire anemometer. In some embodiments, the temperature sensor 128 and flow sensor 130 are in the same sensor housing. The temperature sensor 128 and flow sensor 130 can be connected to the humidifier 104 via connector 132. Additional sensors may be incorporated into the surgical humidification system 100, for example, for sensing parameters at the patient end of the patient conduit 112.

The humidifier control system 106 can be in communication with the heater plate 122 such that the humidifier control system 106 can control a power delivered to the heater plate 122 and/or control a temperature set point of the heater plate 122. As described further herein, the humidifier control system 106 can determine an amount of power to deliver to the heater plate 122, or a heater plate set point, based at least in part on a flow condition, an operation mode, a flow reading, an outlet temperature reading, a heater plate sensor reading, or any combination of these or other factors.

The surgical humidification system 100 can include a conduit heating wire 134 configured to provide heat to the gases traveling along the patient conduit 112. Gases leaving the outlet 118 of the humidification chamber 116 can have a high relative humidity (e.g., about 100%). As the gases travel along the patient conduit 112 there is a chance that water vapor may condense on the conduit wall, reducing the water content of the gases. To reduce condensation of the gases within the conduit, the conduit heating wire 134 can be provided within, throughout, and/or around the patient conduit 112. Power can be supplied to the conduit heating wire 134 from the humidifier 104 and can be controlled through the humidifier control system 106. In some embodiments, the heating wire 134 is configured to maintain the temperature of the gas flowing through the patient conduit 112. In some embodiments, the conduit heating wire 134 can be configured to provide additional heating of the gas to elevate the gases temperature to maintain the humidity generated by the heated water bath in the humidifier 104.

Example Humidifier Control System

Figure 2:
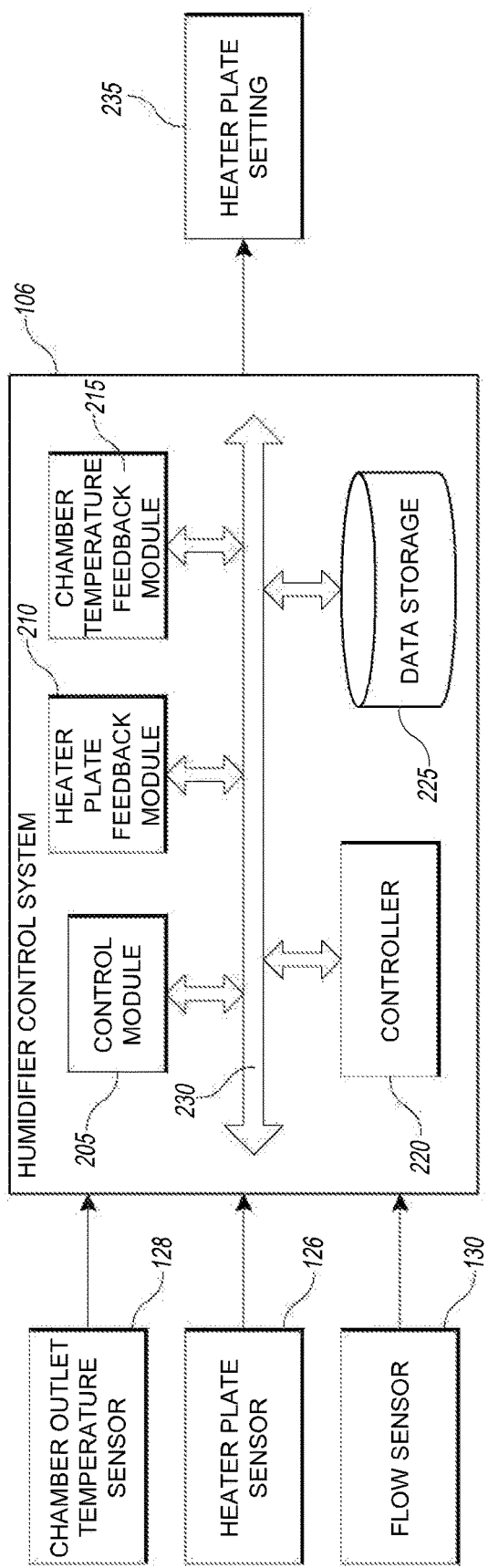
FIG. 2 illustrates a block diagram of an embodiment of a humidifier control system.

FIG. 2 illustrates a block diagram of an example humidifier control system 106. The humidifier control system 106 can include hardware, software, and/or firmware components used to control the humidifier 104. The humidifier control system 106 can be configured to receive information from various sensors or systems, determine a mode of operation based at least in part on the received information, determine a heater plate set point based at least in part on the received information, and control the heater plate 122 to achieve a defined temperature and/or power output. The humidifier control system 106 can include a control module 205, a heater plate feedback module 210, a chamber temperature feedback module 215, a controller 220, and data storage 225. Components of the humidifier control system 106 can communicate with one another, with external systems, and with other components of the humidifier 104 over communication bus 230.

The humidifier control system 106 includes the control module 205 configured to determine a control mode based at least in part on information received regarding the temperature sensor 128, the heater plate 126, the flow sensor 130, user interface elements, or any combination of these. The control module 205 can use the received information to select an appropriate or desired control mode, such as a pre-heat mode, a warm-up mode, an on mode, or other control mode. Based at least in part on the selected control mode, the control module 205 can provide the heater plate feedback module 210 or the chamber temperature feedback module 215 with a set point corresponding to a chamber set point, a heater plate set point, or some combination of these. The set point can be selected based at least in part on the received information and the control mode. For example, the control module 205 can receive a flow rate reading from the flow sensor 130. Based at least in part on the flow rate reading, the control module 205 can determine to control the heater plate 122 using the heater plate feedback module 210 or the chamber temperature feedback module 215. Similarly, the control module 205 can use a variety of conditions to determine a method of control. In some embodiments, the control module 205 uses a flow rate, a chamber outlet temperature, a heater plate reading, a duration of any of a flow condition, a duration of a control mode, or any combination of these to determine an appropriate control mode. For example, the control module 205 can determine that the humidifier is in a high flow state in an open surgery setting when a flow rate exceeds a defined threshold for a defined duration. If the flow rate exceeds the flow rate threshold for the defined duration, the control module 205 can use the chamber temperature feedback module 215 with an input chamber set point to control the heater plate 122. As another example, if the flow rate is below a threshold, the control module 205 can determine to use the heater plate feedback module 210 with a heater plate temperature setting to control the heater plate 122. As another example, if the flow rate is determined to be above a threshold, the control module 205 can use the chamber temperature feedback module 215 to control the heater plate setting, wherein the control module 205 provides the chamber temperature feedback module 215 with a chamber set point corresponding to the flow rate. The received information used by the control module 205 can be used without any additional processing or the information can be processed prior to use. For example, the received information can represent instantaneous values or time-averaged values. The received information can be converted into different units, such as from a received voltage to a corresponding temperature.

The humidifier control system 106 includes the heater plate feedback module 210 configured to control the heater plate 122 in response to input from the heater plate sensor 126. The heater plate feedback module 210 can receive a heater plate temperature set point and control power to the heater plate 122 to achieve the heater plate temperature set point. The heater plate feedback module 210 can be used to control the heater plate 122 when in a defined operation mode or under defined flow conditions, as determined by the control module 205. For example, the heater plate feedback module 210 can receive a heater plate temperature setting from the control module 205, receive a heater plate sensor reading from the heater plate sensor 126 or from the control module 205, and determine a heater plate setting 235 (e.g., whether to apply power to the heater plate 122) based at least in part on a difference between the heater plate temperature setting and the heater plate sensor reading. The heater plate feedback module 210 can use a control loop feedback mechanism to adjust the heater plate setting 235 to achieve a desired set point. The control module 205 can use the heater plate feedback module 210 to control the heater plate 122 until it determines that input from system components (e.g., the chamber temperature sensor 128, heater plate sensor 126, and/or flow sensor 130) warrant using the chamber temperature feedback module 215.

The humidifier control system 106 includes the chamber temperature feedback module 215 configured to control the heater plate 122 in response to input from the chamber outlet temperature sensor 128. The chamber temperature feedback module 215 can be configured to use a feedback control loop that incorporates information from the chamber outlet temperature sensor 128, the heater plate reading 126, the flow sensor 130, or any combination of these to determine a heater plate setting 235. Similar to the heater plate feedback module 210, the control module 205 can use the chamber temperature feedback module 215 to determine a heater plate setting 235 until it determines that input from system components warrant using the heater plate feedback module 210. The chamber temperature feedback module 215 can use a control loop feedback mechanism to adjust the heater plate setting 235 to achieve a desired set point. Adjustments can be made based at least in part on input received from the temperature sensor 128, the flow sensor 130, the heater plate reading 126, or any combination of these.

The heater plate feedback module 210 and the chamber temperature feedback module 215 can use control loop feedback mechanisms to determine a heater plate setting 235 to control the heater plate 122. Parameters of the control loop feedback mechanism can be adjusted to achieve desired results, including, for example, reducing or minimizing gas temperature overshoots or undershoots, increasing efficiency of humidification, providing a consistent humidifier output, decreasing start-up times for humidification, accommodate for varying flow rates, or any combination of these. In some embodiments, the control loop feedback mechanism is a PID controller. In some embodiments, parameters of the PID controller can be selected according to a heater plate setting, a control mode, a flow rate, a user setting, an outlet temperature, a heater plate set point, or any combination of these.

The humidifier control system 106 includes the controller 220 configured to interact with the modules, data storage 225, and external systems of the humidifier 104. The controller 220 can include one or more physical processors and can be used by any of the other components, such as the control module 205, to process information. The humidifier control system 106 includes data storage 225. Data storage 225 can include physical memory configured to store digital information and can be coupled to the other components of the humidifier control system 106, such as the controller 220, the control module 205, the heater plate feedback module 210, and the chamber temperature feedback module 215.

The humidifier control system 106 having the control module 205, the heater plate feedback module 210, and the chamber temperature feedback module 215 can provide flow-dependent control such that heating control can be based on a current flow rate and can be adaptable to changing flow rates during use (e.g., during surgery). For example, the temperature of the gases exiting the chamber 116 can drop if the flow rate of the gases entering and flowing through the chamber 116 increases. The increased flow rate can cause a larger volume of gas to pass through the chamber 116. The larger volume of gases can use more energy from the water vapor, hence leading to a temperature drop as the gases exit. A larger flow rate of gases can use a larger amount of water vapor for the gases to be humidified to a suitable level. The humidifier control system 106 can be configured to compensate for the increased gas flow by increasing the power to the heater base in order to cause more water in the chamber 116 to evaporate such that the gases are humidified to a suitable level. The feedback modules 210 and 215 can be configured to avoid adding an undesirable amount of heat to the chamber 116 through the use of control loop feedback mechanisms, as described herein. This can reduce temperature overshoots which can be undesirable.

The control system 106 can provide control when the chamber 116 contains relatively large volumes of water or when the chamber 116 is an auto-fill chamber, which can be desirable for long-duration surgeries or procedures. The control system 106 can provide therapy specific control through an auto-detect mode or through a user interface element such as a mode button. For example, the control system 106 can be configured to detect whether the humidifier 104 is being used for open surgery or laparoscopic surgery based at least in part on a duration of a high flow rate, and control the heater plate 122 accordingly. The control system 106 can be configured to deliver a desired or defined level of humidity through the use of feedback from the chamber outlet temperature sensor 128, the heater plate sensor 126, and/or the flow sensor 130. By controlling the humidifier 104 using this feedback, the risk of undesirable heat being delivered to the patient can be reduced or eliminated.

The following sections provide non-limiting examples of humidification controls:

Variable Flow Rates

Figure 3:
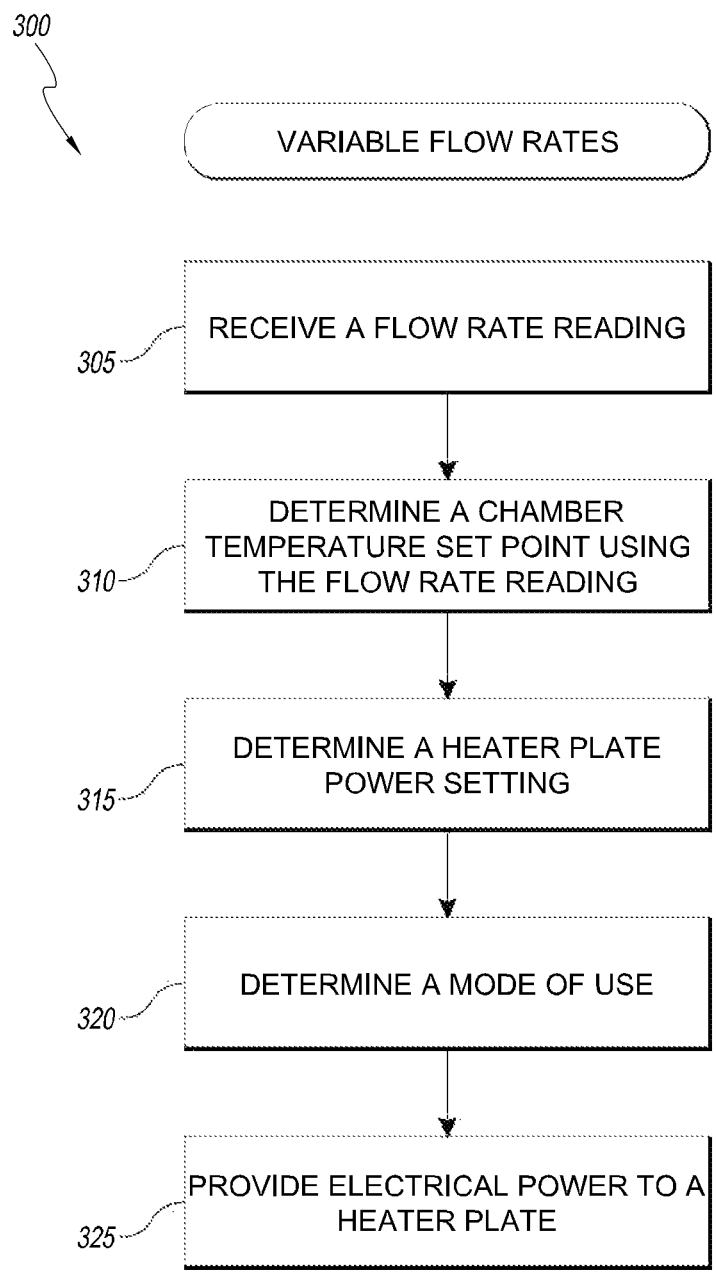
FIG. 3 illustrates a flow chart of an example method of controlling a humidifier to provide for a consistent output by accounting for changes in flow rate.

FIG. 3 illustrates a flow chart of an example method 300 for controlling a humidifier to provide for a consistent output by accounting for changes in flow rate. The humidifier 104 can adjust heater plate settings to account for changes in the flow rate which can cause inefficiencies in the humidification process. For example, at flow ranges typical in a laparoscopic procedure (e.g. between about 0 and 15 liters per minute (Lpm)), the efficiency of the humidifier 104 can vary across the flow range. In some embodiments, for a given water temperature inside the chamber 116, the output temperature and humidity of the gas will decrease as flow rate increases. The method 300 can be used to provide a consistent output humidity and/or temperature by controlling the heater plate such that an amount of power delivered to the heater plate 122 is based at least in part on the flow rate of the gas. For ease of description, the steps in the method 300 are described as being performed by the humidifier control system 106. However, any step or combination of steps in the method 300 can be performed by any component of the humidifier control system 106, any combination of components of the humidifier control system 106, or any component or combination of components of the humidifier 104 or surgical humidification system 100.

In block 305, the humidifier control system 106 receives a flow rate reading from the flow sensor 130. The flow rate reading can be processed according to processing instructions in the humidifier control system 106. In some embodiments, the humidifier control system 106 monitors the flow sensor, receiving multiple flow rate readings. The frequency of readings can depend at least in part on the humidifier control system 106, the flow sensor 130, or other factors or combination of factors. In some embodiments, the flow rate reading corresponds to an average of multiple flow sensor values over time. Using the time-averaged flow rate can reduce or eliminate fluctuations in power supplied to the heater plate 122 by the humidifier control system 106 in response to the flow rate readings. The time over which the average flow rate reading is taken can be configured to reduce or eliminate small-scale fluctuations and to be responsive to changes in flow rates.

In block 310, the humidifier control system 106 determines a chamber temperature set point based at least in part on the flow rate reading. The chamber temperature set point can correspond to a range of flow rates such that there is a single, defined chamber temperature set point corresponding to any flow rate between a lower flow rate and an upper flow rate. There can be multiple chamber set points corresponding to multiple flow rate ranges. In some embodiments, the chamber temperature set point is an output of a real-valued function of the flow rate. In some embodiments, the chamber temperature set point is an output of a discrete-valued function of the flow rate. In some embodiments, the chamber temperature set point is a function of the flow rate and other variables. By determining the chamber temperature set point based at least in part on the flow rate reading, the humidifier 104 can be configured to experience a slowed response to rapidly changing flows where fluctuations in flow result in little or no fluctuations in power output to the heater plate 122. Temperature overshoots may happen in a case where the flow rate temporarily increases and the humidifier control system 106 responds to the increase by increasing the heater plate power. The humidifier 104 can be configured to reduce or eliminate temperature overshoots when a flow rate subsequently reduces by limiting an amount of added power at higher flows. Avoiding temperature overshoots can be desirable because cooling the water in the humidifier 104 can be difficult and/or time intensive.

In block 315, the humidifier control system 106 determines an amount of power to be applied to the heater plate 122 based at least in part on a difference between a chamber outlet temperature reading and the chamber temperature set point. As described above, the humidifier control system 106 can use a control loop feedback mechanism to determine a chamber temperature set point. The control loop feedback mechanism can accept as input the chamber temperature set point, the chamber temperature reading, and the heater plate power and output a new heater plate power setting based at least in part on a difference between the chamber temperature set point and the chamber temperature reading. The control loop feedback mechanism can incorporate current measurements in addition to previous measurements to improve or optimize control of the temperature and/or humidity of the gas.

In block 320, the humidifier control system 106 determines a mode of use. The mode of use can correspond to, for example, use in conjunction with open surgery, a laparoscopic procedure, an endoscopic procedure, or the like. The chamber temperature set point can be altered based on the mode of use. For example, the humidifier control system 106 can have different sets of chamber temperature set points for laparoscopic and open surgery.

In block 325, the humidifier control system 106 provides an amount of electrical power to the heater plate 122, the amount of power based at least in part on the flow rate reading and the mode of operation. The humidifier control system 106 can update the amount of electrical power provided to the heater plate 122 based at least in part on an updated flow rate reading, an updated mode of use, or a combination of both of these.

Low Flow Rates

Figure 4:
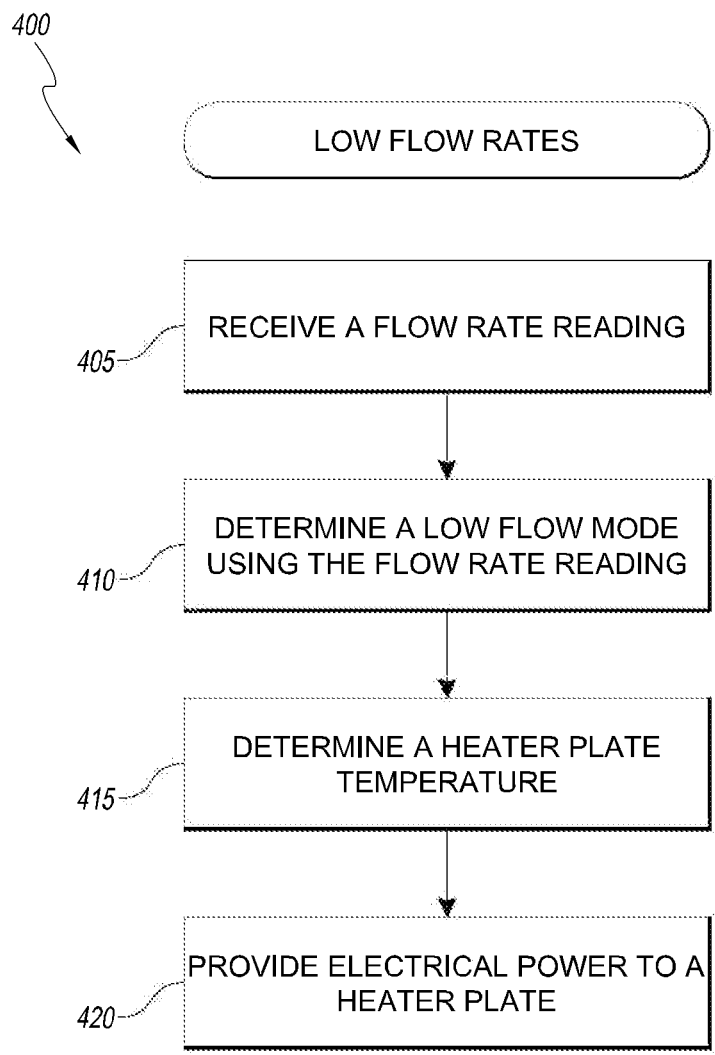
FIG. 4 illustrates a flow chart of an example method of controlling a humidifier in a low flow mode.

FIG. 4 illustrates a flow chart of an example method 400 of controlling a humidifier 104 when a flow rate of the gas is relatively low (e.g., less than or equal to about 3 Lpm, less than or equal to about 2 Lpm, less than or equal to about 1 Lpm, or less than or equal to about 0.5 Lpm). The method 400 can compensate for difficulties in acquiring accurate temperature information in the chamber outlet 118 of the humidifier 104 arising from relatively small amounts of gas passing over the chamber outlet temperature sensor 128. The method 400 can use other sensors in addition to the chamber outlet temperature sensor 128 to control the humidifier 104 at relatively low flows or at flows where the chamber outlet temperature sensor 128 may provide temperature information that is less accurate than desired.

At relatively low flow rates, the chamber temperature sensor 128 can return inaccurate temperature readings that tend to be lower than the actual temperature of the gas. This can cause the humidifier control system 106 to increase power to the heater plate 122 to compensate for this apparent drop in temperature. To reduce or avoid undesirable increases in power delivered to the heater plate 122, the humidifier control system 106 can use the method 400 to switch the humidifier 104 into a low-flow state where the chamber outlet temperature is not used to control the heater plate 122. The humidifier control system 106 can use, for example, the output from a temperature sensor located at the heater plate to control the heater plate 122 to maintain the heater plate 122 at a particular temperature. As a result, when flow increases over a defined flow threshold, the humidifier control system 106 can again use the chamber outlet temperature sensor 128 to control the humidifier 104 thereby reducing or eliminating excessive temperature overshoot. For ease of description, the steps in the method 400 are described as being performed by the humidifier control system 106. However, any step or combination of steps in the method 400 can be performed by any component of the humidifier control system 106, any combination of components of the humidifier control system 106, or any component or combination of components of the humidifier 104 or surgical humidification system 100.

In block 405, the humidifier control system 106 receives a flow rate reading. Similar to the description corresponding to block 305 in FIG. 3, the humidifier control system 106 can monitor the flow sensor and use an instantaneous or a time-averaged value of the flow rate. The flow rate reading can be processed prior to use by the humidifier control system 106.

In block 410, the humidifier control system 106 determines a low flow mode based at least in part on the flow rate reading. The low flow mode can be determined where the flow rate reading is less than or equal to a defined threshold. The defined threshold can be less than or equal to about 3 Lpm, less than or equal to about 2 Lpm, less than or equal to about 1 Lpm, less than or equal to about 0.5 Lpm. The humidifier control system 106 can determine a normal mode when the flow rate reading exceeds the defined threshold.

In block 415, the humidifier control system 106 determines a heater plate temperature set point. In some embodiments, the humidifier control system 106 uses a heater plate temperature set point in the low flow mode rather than a chamber temperature set point because at low flow rates the chamber outlet temperature produces unstable results and/or produces readings that have an accuracy that is less than desirable. The humidifier control system 106 can use a control loop feedback mechanism to determine a heater plate power based at least in part on a difference between the heater plate temperature set point and a heater plate temperature reading. For example, if the heater plate temperature reading is less than the heater plate set point, power can be applied to the heater plate 122. If the heater plate temperature is greater than or equal to the heater plate set point, power can be removed from the heater plate 122. In some embodiments, the heater plate temperature set point can be at least about 36 degrees and/or less than or equal to about 60 degrees, at least about 36 degrees and/or less than or equal to about 50 degrees, at least about 36.5 degrees and/or less than or equal to about 40 degrees, or about 37 degrees.

In block 420, the humidifier control system 106 provides electrical power to the heater plate 122 based on the low-flow mode. The power provided to the heater plate 122 can change if the flow rate reading exceeds the defined threshold and the humidifier 104 enters a normal mode of operation.

Pre-Heat Mode

Figure 5:
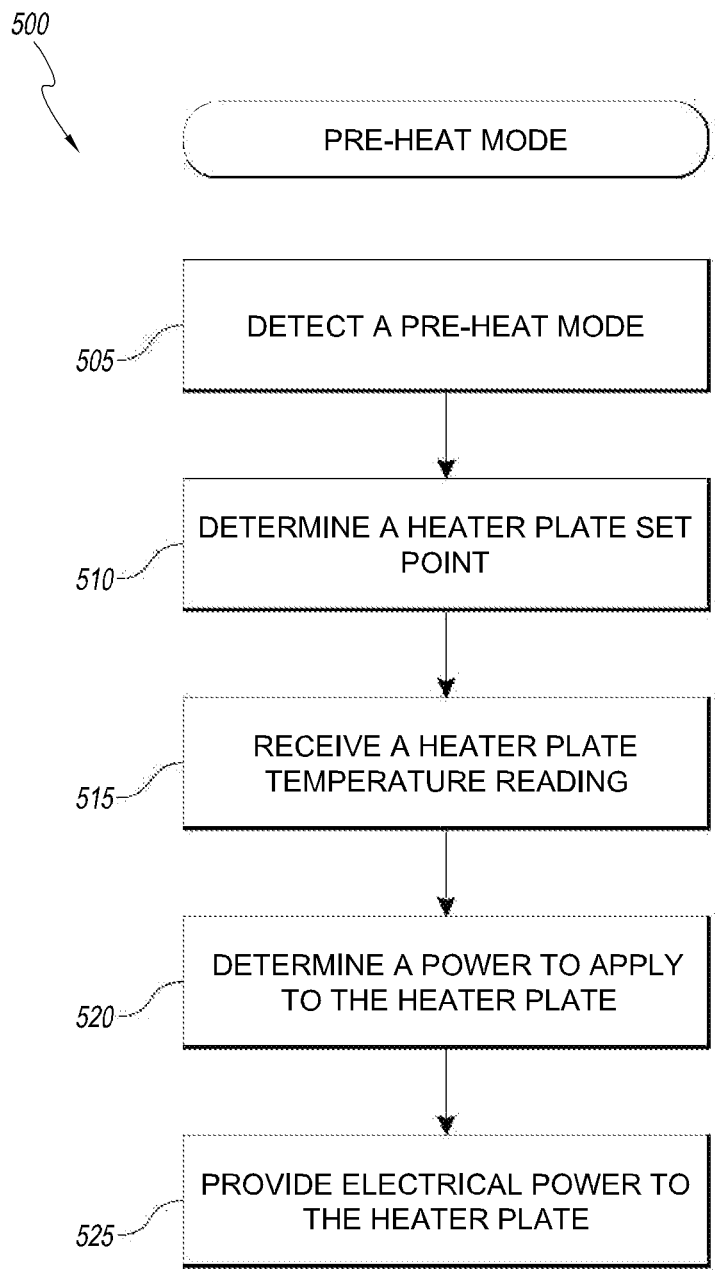
FIG. 5 illustrates a flow chart of an example method of controlling a humidifier in a pre-heat mode.

FIG. 5 illustrates a flow chart of an example method 500 of controlling a humidifier in a pre-heat mode. In some surgical procedures, there can be a relatively long delay between a time at which the humidifier 104 is set up and a time that gas flow to the patient 102 commences. If the humidifier 104 is left off until gas flow starts, the humidifier 104 can output a low temperature until the humidifier 104 warms up. If the humidifier 104 is left on until gas flow starts, the humidifier 104 can output a gas having an elevated temperature due at least in part to the chamber output temperature sensor 128 being unable to read the gas flow temperature when there is no gas flow. The humidifier control system 106 can use the method 500 to determine a heater plate set point to power the heater plate 122 when the humidifier 104 is turned on, thereby enabling the humidifier to stay warm and ready for gas flow to start. For ease of description, the steps in the method 500 are described as being performed by the humidifier control system 106. However, any step or combination of steps in the method 500 can be performed by any component of the humidifier control system 106, any combination of components of the humidifier control system 106, or any component or combination of components of the humidifier 104 or surgical humidification system 100.

The pre-heat mode can be used with the humidifier 104 that is configured to be used in conjunction with laparoscopic procedures as well as open surgery. Due at least in part to the constant high gas flow used in open surgery, the humidifier control system 106 can use a relatively aggressive control algorithm to achieve an desirable warm-up time. However, this type of algorithm can result in excessive instability during laparoscopic procedures which may lead to unwanted temperature overshoots. Thus, to avoid using the aggressive algorithm and still achieve a desirable warm-up time during open surgery, the humidifier control system 106 can use the method 500 to operate the humidifier 104 according to the pre-heat mode. The pre-heat mode allows the humidifier 104 to be partially set up with only the chamber 116 filled with water attached and without the conduits 110, 112 attached. When the humidifier 104 is switched on in this partially set up state, the humidifier control system 106 can detect this and automatically enter the pre-heat mode. In the pre-heat mode, the humidifier control system 106 uses the heater plate temperature instead of the chamber outlet temperature to control power to the heater plate 122 to achieve a heater plate temperature set point. As such, the pre-heat mode allows the heater plate to receive power and to be switched on prior to commencement of the open or laparoscopic procedure to allow time for the chamber to warm up. Once the procedure is ready to commence, set up of the surgical humidification system 100 can be completed (e.g., connecting the patient conduit 112 from the patient 102 to the outlet port 118 and/or connecting the inlet conduit 110 from the gas source 108 to the inlet port 114). The humidifier control system can automatically detect the completed set up at which point the humidifier control system 106 can switch out of pre-heat mode and enter a normal run mode. In some embodiments, warm-up time is reduced to less than 10 minutes for both open and laparoscopic procedures when utilizing the pre-heat mode for about 5 minutes.

In block 505, the humidifier control system 106 detects a pre-heat mode. The pre-heat mode can be where the chamber 116 is coupled to the humidifier body 124 such that the heater plate 122 is in contact with the metal base 121. The pre-heat mode can be where the chamber 116 is coupled to the humidifier body 124 and the chamber contains a defined amount of water. The pre-heat mode can be where the chamber 116 is at least partially filled with water and is coupled to the humidifier body 124 and the inlet conduit 110, the patient conduit 112, or both are disconnected from the chamber 116. In some embodiments, the pre-heat mode can be selected by a user using a user interface element.

In block 510, the humidifier control system 106 determines a heater plate temperature set point. In some embodiments, the heater plate temperature set point is a constant value in the pre-heat mode. In block 515, the humidifier control system 106 receives a heater plate temperature from the heater plate sensor 126. In block 520, the humidifier control system 106 determines a power to apply to the heater plate 122 based at least in part on the heater plate temperature set point and the heater plate temperature reading. In some embodiments, the humidifier control system 106 uses a control loop feedback mechanism to determine a power to apply to the heater plate 122. For example, the humidifier control system 106 can determine to apply power to the heater plate 122 when the heater plate temperature reading is less than the heater plate temperature set point. In some embodiments, the amount of power applied is proportional to the difference between the heater plate temperature set point and the heater plate temperature reading.

In block 525, the humidifier control system 106 provides electrical power to the heater plate 122. In some embodiments, the humidifier control system 106 is configured to detect when the pre-heat mode no longer applies and to operate in a normal mode. The pre-heat mode can be terminated where the inlet conduit 110 and the patient conduit 112 are connected to the chamber 116 and the chamber is coupled to the humidifier body 124. In the normal mode, the humidifier control system 106 can control the amount of power to the heater plate 122 based at least in part on a flow rate reading, a mode of use, a chamber outlet temperature, a heater plate temperature, or any combination of these as described herein with reference to FIG. 3 or 4.

Procedure Mode of Use

Figure 6:
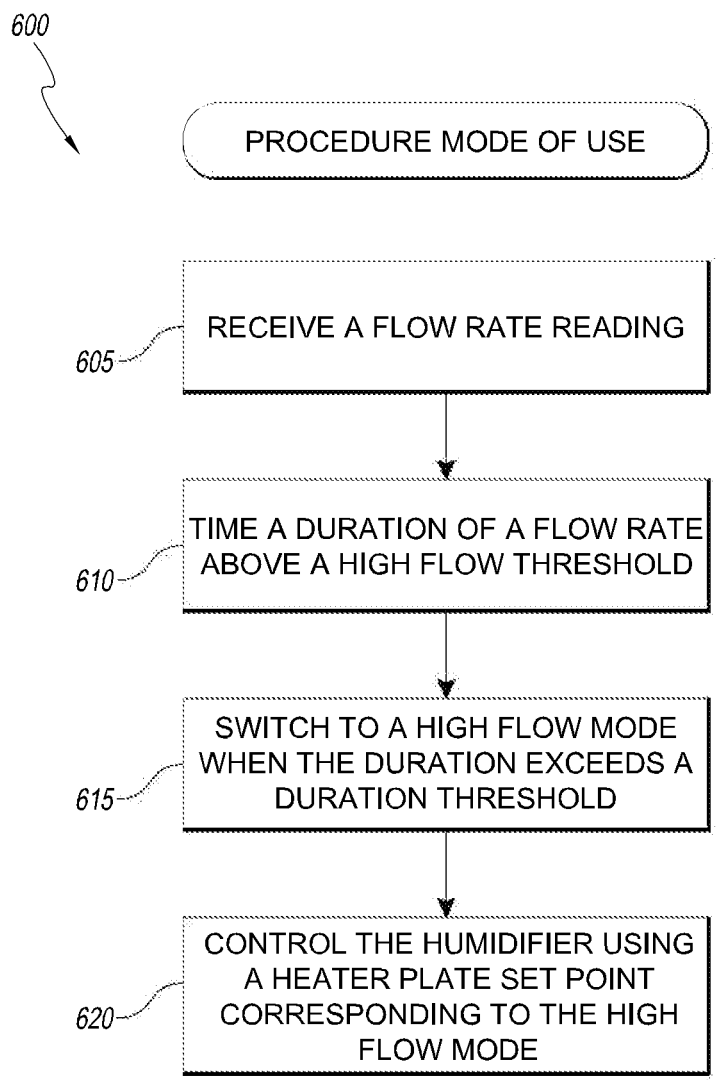
FIG. 6 illustrates a flow chart of an example method of controlling a humidifier to adjust control properties according to a mode of operation.

FIG. 6 illustrates a flow chart of an example method 600 of controlling a humidifier to adjust control properties according to a mode of use. The humidifier 104 can be used in laparoscopic procedures, endoscopic procedures, open surgery, and the like. Open surgery can use a relatively high, constant flow rate (e.g., greater than about 15 Lpm) compared to laparoscopic surgery flow rates (e.g., varying between about 0 and 15 Lpm). Differing control modes can be used for the different procedures due at least in part to this difference in consistency and magnitude of flow rates. The humidifier control system 106 can use the method 600 to detect which mode of use is being employed and change control algorithms accordingly. The humidifier control system 106 can detect an open surgery mode of use when the flow rate reading exceeds a defined threshold for a defined duration. The defined threshold and duration can be selected such that it is improbable that a laparoscopic procedure would use a flow rate exceeding the defined threshold for the defined duration.

In block 605, the humidifier control system 106 receives a flow rate reading. Similar to the description corresponding to block 305 in FIG. 3, the humidifier control system 106 can monitor the flow sensor and use an instantaneous or a time-averaged value of the flow rate. The flow rate reading can be processed prior to use by the humidifier control system 106. In some embodiments, the humidifier control system 106 can receive flow rate readings on a nearly continuous basis. This can enable the humidifier control system 106 to monitor the flow rate readings over time.

In block 610, the humidifier control system 106 times a duration of a flow rate above a high flow threshold. In some embodiments, to distinguish between open and laparoscopic procedures automatically, the humidifier control system 106 can begin a timer once a high flow state is detected. Detecting a high flow state can comprise receiving a flow rate reading that exceeds the high flow threshold. In some embodiments, the high flow threshold is at least about 7 Lpm, at least about 10 Lpm, at least about 12 Lpm, at least about 15 Lpm, or at least about 20 Lpm. The timer can continue to run as long as the flow remains above the high flow threshold. If the flow reduces below the high flow threshold, the timer can be reset. The timer can restart if the flow rate reading once again exceeds the high flow threshold.

In block 615, the humidifier control system 106 controls the heater plate 122 according to a high flow mode when the flow rate exceeds the high flow threshold for a duration threshold. In some embodiments, the duration threshold is at least about 1 minute, at least about 2 minutes, at least about 3 minutes, or at least about 5 minutes. Because flow rates temporarily exceeding the high flow threshold can be used in laparoscopic procedures, the duration threshold can be configured to be long enough to exclude typical temporary increases in flow rate in laparoscopic procedures. To reduce or avoid temperature overshoots that may occur after high flow periods during laparoscopic surgery, the chamber temperature set point can be reduced compared to the chamber temperature set point for open surgery. As a result, short periods of high flow in laparoscopic surgery may not result in the humidifier control system 106 providing undesirable power to the heater plate that may result in temperature overshoots when the flow reduces again. However, for open surgery the humidifier control system 106 can be configured to automatically provide a desirable quantity of power to the heater plate 122 to sustain a desired temperature and/or humidity for the high flow rates used. In some embodiments, the chamber temperature set point is set to a value of at least about 36 degrees and/or less than or equal to about 60 degrees, at least about 36 degrees and/or less than or equal to about 50 degrees, at least about 36.5 degrees and/or less than or equal to about 40 degrees, at least about 36.5 degrees and/or less than or equal to about 37.5 degrees, or about 37 degrees. If after switching to the high flow mode the flow rate readings drop below the high flow threshold, the humidifier control system switches to a normal mode of operation and the timer can be reset. The normal mode of operation can be similar to the modes of operation described herein with reference to FIGS. 3 and 4.

In block 620, the humidifier control system 106 controls the humidifier 104 using a chamber temperature set point when in the high flow mode. In some embodiments, the chamber temperature set point in the high flow mode is different from the chamber temperature set point in the normal flow mode. The humidifier control system 106 can be configured to apply an amount of power to the heater plate 122 based at least in part on a difference between a chamber temperature set point and a chamber temperature reading, similar to the methods described herein with reference to FIG. 3. When not in the high flow mode, the humidifier control system 106 can control the humidifier 104 using a chamber temperature set point or a heater plate temperature set point, as described herein with reference to FIGS. 3 and 4. In some embodiments, a high flow mode and/or a normal mode can be selected by a user using a user interface element.

In some embodiments, the mode of use can be automatically detected without using a flow rate. The automatic detection can comprise utilizing a timer to time how long it takes to reach a temperature set point based on a heating energy delivered to the heater plate 122. It can take longer to reach the temperature set point at relatively constant high flow rates (e.g., similar to flow rates used for open surgery) than at variable low flow rates (e.g., similar to flow rates used for laparoscopic surgery).

Example of a Control System and Method

Figure 7A:
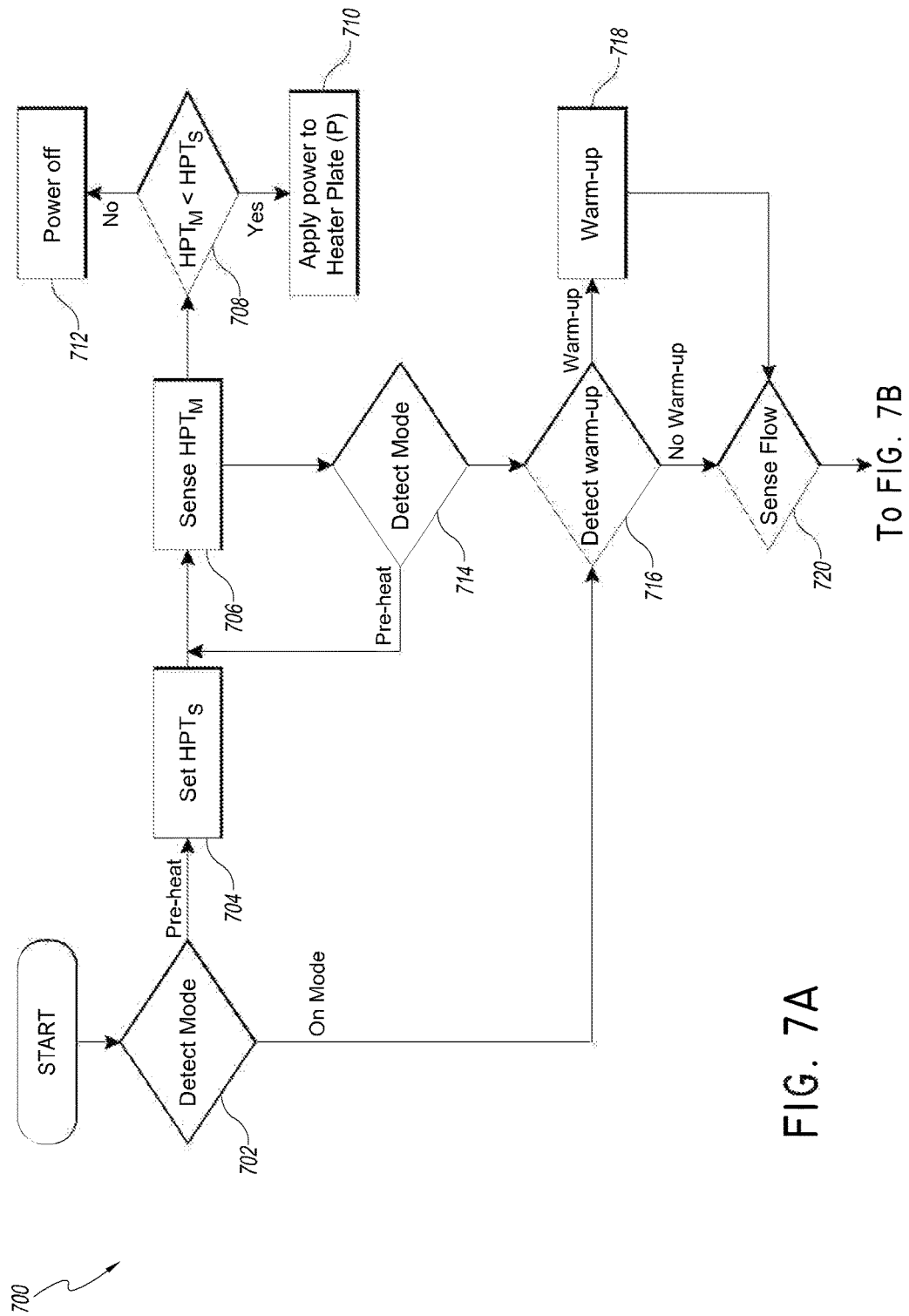
FIGS. 7A-C illustrate a flow chart of an example method for controlling a humidifier.
Figure 7B:
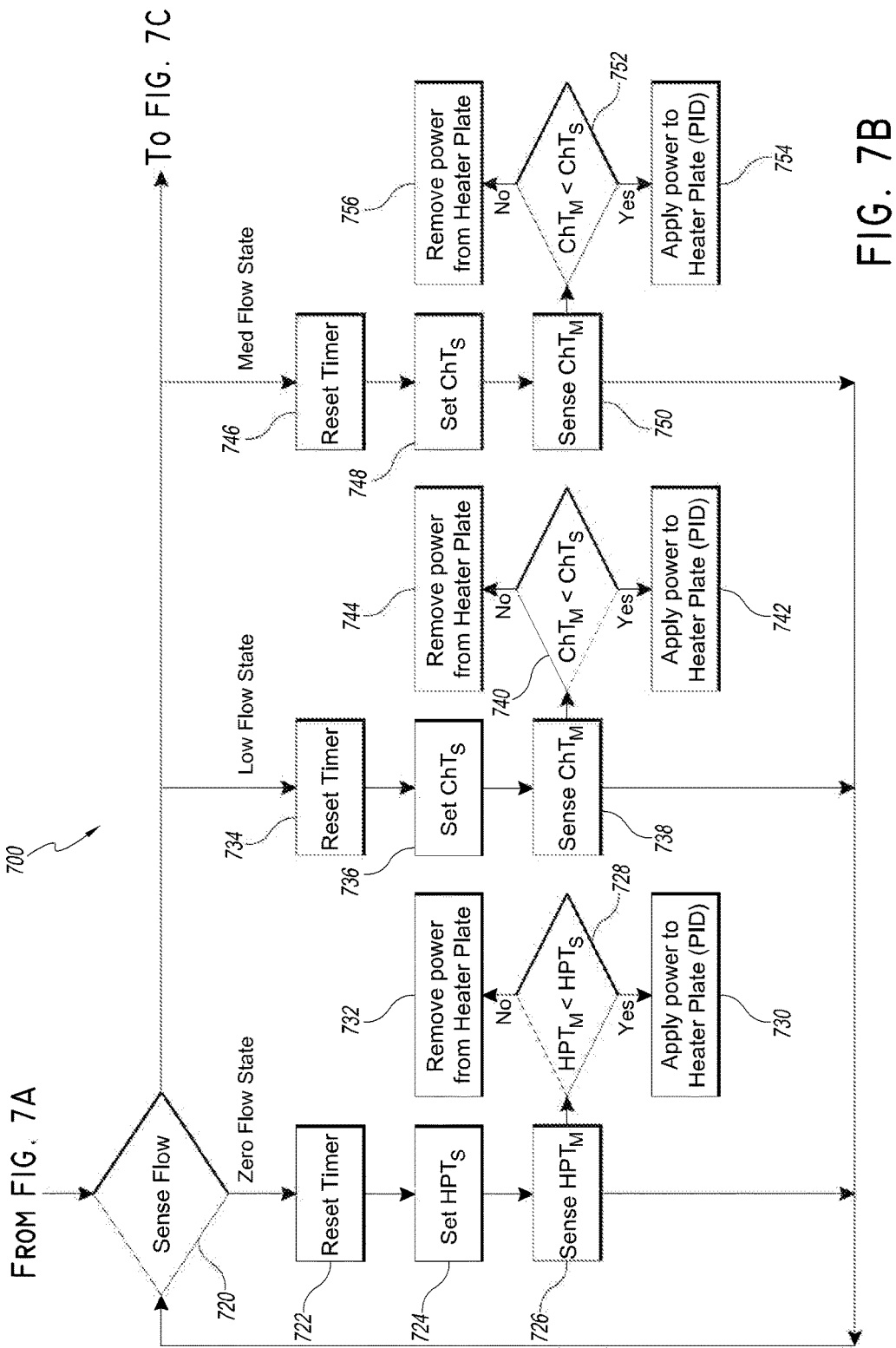
Figure 7C:
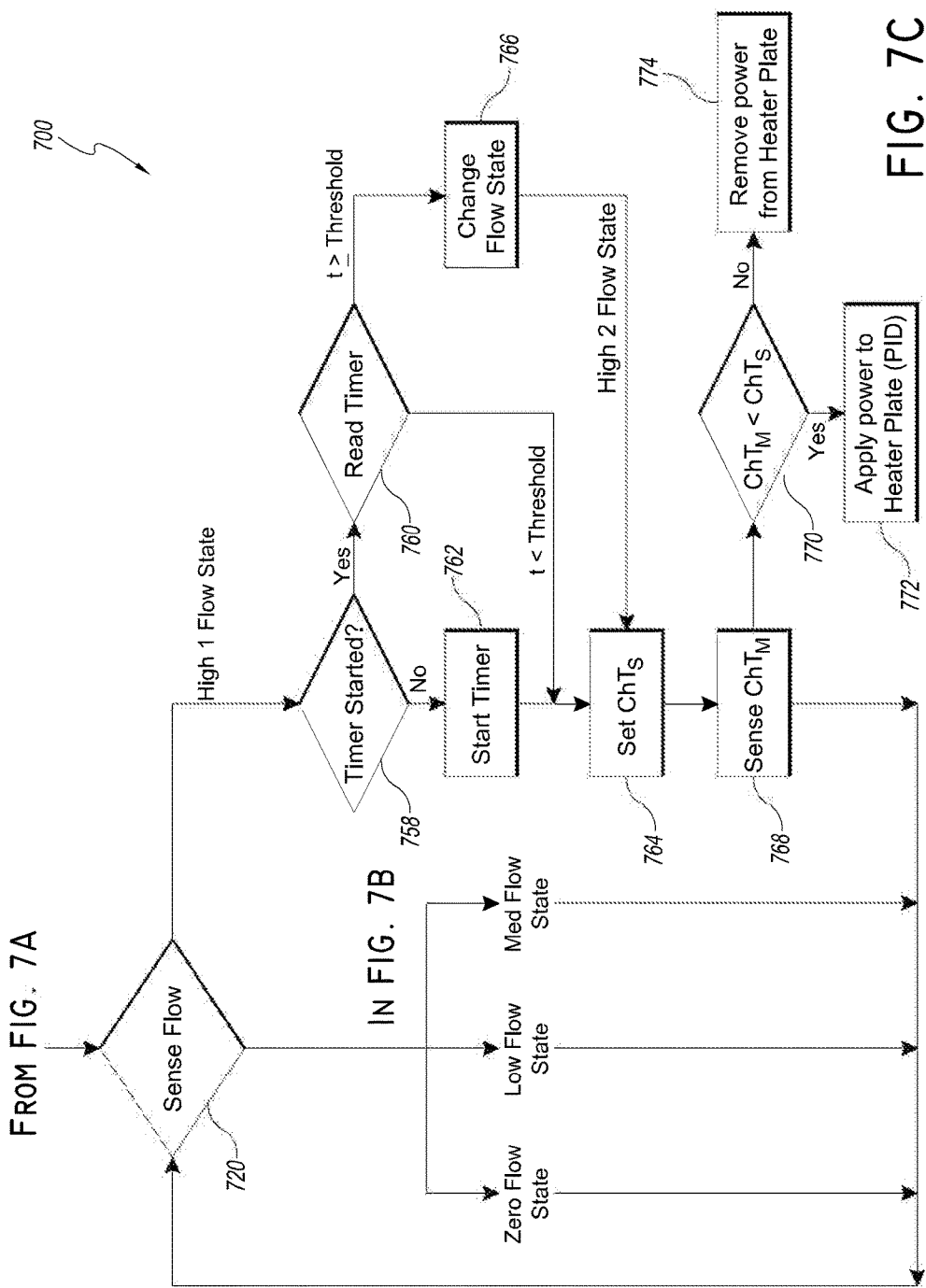

FIGS. 7A-C illustrate a flow chart of an example method 700 for controlling a humidifier 104. The example method 700 incorporates elements from the example control methods described herein with reference to FIGS. 3-6. The example method 700 illustrated in the flow charts in FIGS. 7A-C represents an example embodiment of a method 700 to be implemented in the humidifier control system 106 to control the humidifier 104.

As illustrated in FIG. 7A, the method 700 begins in block 702 with detecting a mode of operation. The mode of operation can be a pre-heat mode or an on mode. The pre-heat mode is similar to the method described herein with reference to FIG. 5 and can be automatically detected based at least in part on a configuration of the humidifier and/or through a user selection. If the humidifier control system 106 detects a pre-heat mode, the system 106 sets a heater plate temperature set point ($HPT_S$) in block 704. In block 706, the humidifier control system 106 measures a heater plate temperature ($HPT_M$). In block 708, the humidifier control system 106 compares the measured temperature to the set point and determines whether to apply power to the heater plate 122 in block 710, or to apply no power to the heater plate 122 in block 712. In some embodiments, the humidifier control system 106 can determine an amount of power to apply to the heater plate 122 based at least in part on a difference between the set point and the measurement, where the amount of power is proportional to the difference (represented by the "(P)" in block 710). In some embodiments, the humidifier control system 106 determines the amount of power using a PID controller. In block 714, the humidifier control system 106 detects whether the humidifier 104 remains in a pre-heat mode. If so, the humidifier control system 106 returns to block 706 to measure the heater plate temperature. If the humidifier control system 106 detects that the humidifier 104 is in an on mode in block 702, it moves to block 716 to detect if the humidifier 104 warrants a warm-up mode.

In block 716 the humidifier control system 106 detects whether the humidifier 104 warrants a warm-up mode. If the humidifier warrants a warm-up mode, the humidifier control system 106 moves to block 718 and controls power to the heater plate 122 according to the warm-up mode. If no warm-up mode is warranted, the humidifier control system 106 moves to block 720 to sense a flow rate of gases through the humidifier 104.

FIG. 7B illustrates a second portion of the method 700 for controlling the humidifier 104. In block 720, the humidifier control system 106 detects flow rate readings from the flow sensor 130. Based at least in part on the flow sensor readings, the humidifier control system 106 enters a defined control state. In a first control state, identified in FIG. 7B as the "Zero Flow State," the humidifier control system 106 resets a timer in block 722, the timer corresponding to a high flow mode timer described with reference to FIG. 6. In block 724, the humidifier control system sets a heater plate temperature set point and in block 726 it measures a heater plate temperature. In block 728 the humidifier control system 106 compares the heater plate temperature set point to the heater plate temperature measurement. If the measurement is less than the set point, the humidifier control system 106 applies power to the heater plate 122 in block 730. In some embodiments, the amount of power applied to the heater plate 122 is determined using a PID feedback controller (identified as "PID" in block 730). If the measurement is greater than or equal to the set point, the humidifier control system 106 removes power from the heater plate 122 in block 732. The humidifier control system 106 then returns to block 720 to detect the flow rate.

In a second control state, identified in FIG. 7B as the "Low Flow State," the humidifier control system 106 resets a timer in block 734, the timer corresponding to a high flow mode timer described with reference to FIG. 6. In block 736, the humidifier control system sets a chamber outlet temperature set point ($ChT_S$) and in block 738 it measures a chamber outlet temperature ($ChT_M$). In block 740 the humidifier control system 106 compares the chamber outlet temperature set point to the chamber outlet temperature measurement. If the measurement is less than the set point, the humidifier control system 106 applies power to the heater plate 122 in block 742. In some embodiments, the amount of power applied to the heater plate 122 is determined using a PID feedback controller (identified as "PID" in block 742). If the measurement is greater than or equal to the set point, the humidifier control system 106 removes power from the heater plate 122 in block 744. The humidifier control system 106 then returns to block 720 to detect the flow rate.

In a third control state, identified in FIG. 7B as the "Med Flow State," the humidifier control system 106 follows the same sequence of events described for the "Low Flow State," except the chamber outlet temperature set point may be different, as described herein with reference to Table 1. In block 746, the humidifier control system resets a timer. In block 748, the humidifier control system sets a ChTS. In block 750, the humidifier control system senses a ChTM. In block 752, the humidifier control system determines if ChTM is lower than ChTS. If ChTM is lower than ChTS, the humidifier control system applies power to the heater plate in block 754. If ChTM is not lower than ChTS, the humidifier control system removes power from the heater plate in block 756. The humidifier control system then returns to block 720 to detect the flow rate. Furthermore, as described herein, the "Med Flow State" and the "Low Flow State" can differ with regard to the conditions for entering the control states, as described herein with reference to FIG. 8.

FIG. 7C illustrates flow charts for a fourth and fifth control state. The fourth control state is identified as "High 1 Flow State" in FIG. 7C. If the humidifier control system 106 enters the fourth control state in response to the flow rate readings, it checks whether the high flow timer has started in block 758. If the timer has already started, the humidifier control system 106 reads the timer in block 760. If the timer has not already started (e.g., it has been previously reset in other control states), the timer is started in block 762. The timer starts when a flow rate reading exceeds the high flow threshold, as described herein with reference to FIG. 6. If the timer is read and it has a value less than the duration threshold, the humidifier control system moves to block 764 to set a chamber outlet temperature set point. If the timer is greater than or equal to the duration threshold, the humidifier control system 106 changes control states in block 766, from "High 1 Flow State" to "High 2 Flow State." The "High 2 Flow State" can correspond to a control state used in conjunction with open surgery, where flow rates are relatively constant and exceed the high flow threshold for times longer than the high flow duration. Upon changing the control state, the humidifier control system 106 moves to block 764 to set a chamber outlet temperature set point. The chamber outlet temperature set points can be different for the different states, as described herein with reference to Table 1. Once the chamber outlet temperature set point is set, the humidifier control system 106 controls the heater plate 122 according to the methods described in the second and third control states corresponding to the "Low Flow State" and the "Med Flow State" described with reference to FIG. 7B. In block 768, the humidifier control system senses a ChTM. In block 770, the humidifier control system determines if ChTM is lower than ChTS. If ChTM is lower than ChTS, the humidifier control system applies power to the heater plate in block 772. If ChTM is not lower than ChTS, the humidifier control system removes power from the heater plate in block 774. The humidifier control system 106 then returns to block 720 to receive a flow rate reading.

Figure 8:
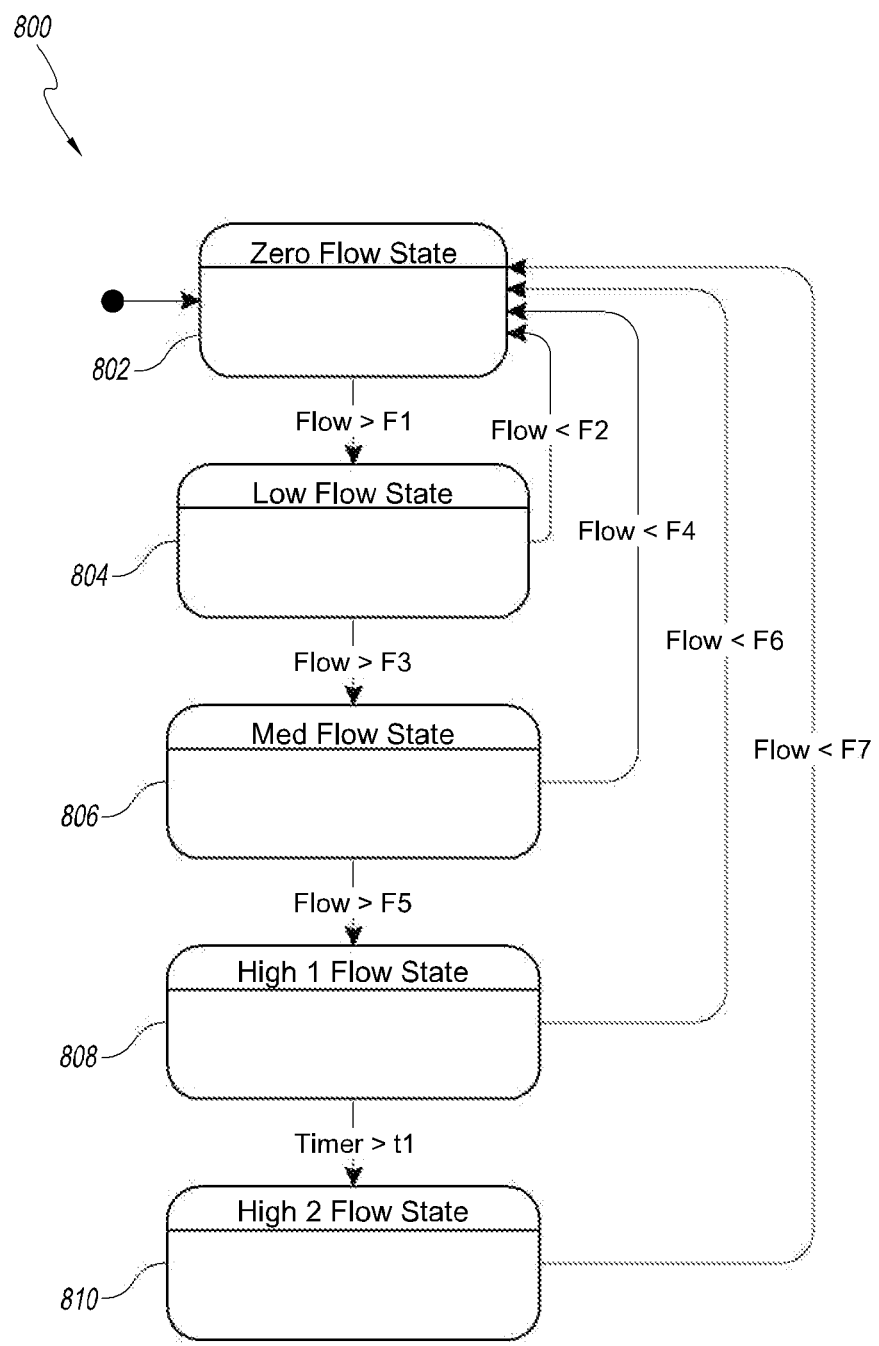
FIG. 8 illustrates a state chart corresponding to a method of determining a control state that can be implemented in an example embodiment of a control module.

FIG. 8 illustrates a state chart 800 corresponding to a method of determining a control state that can be implemented in an example embodiment of a control module 205. The control module 205 of the humidifier control system 106 can use flow rate readings to determine a control state or mode, examples of which are described with reference to FIGS. 3, 4, and 7A-C. For example, the state chart 800 is initiated in the "Zero Flow State" 802. If the flow rate exceeds flow F1 while in the "Zero Flow State" 802, the control module 205 moves to the "Low Flow State" 804. In some embodiments, the flow F1 can be about 1 Lpm. If the flow rate drops below flow F2 or exceeds flow F3 while in the "Low Flow State" 804, the control module 205 moves to the "Zero Flow State" 802 or the "Med Flow State" 806, respectively. In some embodiments, the flow F2 can be about 1 Lpm and flow F3 can be about 3 Lpm. If the flow rate drops below flow F4 or exceeds flow F5 while in the "Med Flow State" 806, the control module 205 moves to the "Zero Flow State" 802 or the "High 1 Flow State" 808, respectively. In some embodiments, the flow F4 can be about 2 Lpm and flow F5 can be about 5.5 Lpm. If the flow rate drops below flow F6 while in the "High 1 Flow State" 808 or if the control module 205 is in the "High 1 Flow State" 808 for a time that exceeds time t1, the control module 205 moves to the "Zero Flow State" 802 or the "High 2 Flow State" 810, respectively. In some embodiments, the flow F6 can be about 4.5 Lpm. In some embodiments, the time t1 can be about 3 minutes. If the flow rate drops below flow F7 while in the "High 2 Flow State" 810, the control module 205 moves to the "Zero Flow State" 802. In some embodiments, the flow F7 can be about 7 Lpm.

In some embodiments, the control module 205 controls the humidifier 104 through the heater plate feedback module 210 when in the "Zero Flow State" 802. As described herein, the heater plate feedback module 210 uses a heater plate temperature set point and a heater plate temperature reading to control power to the heater plate 122. In some embodiments, the control module 205 controls the humidifier 104 through the chamber temperature feedback module 215 when in any state besides the "Zero Flow State" 802. As described herein, the chamber temperature feedback module 215 uses a chamber outlet temperature set point and a chamber outlet temperature reading to control power to the heater plate 122.

Table 1 lists example chamber set points corresponding to different control states. For example, when the humidifier control system 106 is in the "Zero Flow State" there is no chamber set point and the humidifier control system 106 controls the heater plate 122 using a fixed heater plate temperature T0, as described herein. In some embodiments, the fixed heater plate temperature T0 can be about 37 degrees. When the humidifier control system 106 is in the "Low Flow State," the "Med Flow State," the "High 1 Flow State," or the "High 2 Flow State" the humidifier control system 106 can use PID feedback control to achieve a chamber set point corresponding to a temperature T1, T2, T3, or T4, respectively. In some embodiments, the chamber outlet temperature set points T1, T2, T3, and T4 are about 37 degrees, about 35 degrees, about 33 degrees, and about 37 degrees, respectively. The "High 2 Flow State" can be used in conjunction with open surgery and the other control states can be used in conjunction with laparoscopic procedures, for example.

TABLE 1

| | Chamber Setpoint | Heater Plate | Therapy |
|---|---|---|---|
| Zero Flow State | No set point | Fixed heater plate temperature T0 | Laparoscopic |
| Low Flow State | Temperature T1 | PID feedback controlled heater plate to achieve set point | |
| Med Flow State | Temperature T2 | | |
| High 1 Flow State | Temperature T3 | | |
| High 2 Flow State | Temperature T4 | | Open surgery |

Examples of humidifier control systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate principles controlling a surgical humidifier, and details regarding divisions of modules or systems have been provided for ease of description rather than attempting to delineate separate physical embodiments. The examples and figures are intended to illustrate and not to limit the scope of the inventions described herein. For example, the principles herein may be applied to a surgical humidifier as well as other types of humidification systems, including respiratory humidifiers. The principles herein may be applied in laparoscopic surgery or open surgery as well as in other scenarios, such as endoscopic procedures and/or other minimally invasive surgical procedures.

As used herein, the term "processor" refers broadly to any suitable device, logical block, module, circuit, or combination of elements for executing instructions. For example, the controller 220 can be any conventional general purpose single- or multi-chip microprocessor such as a Pentium® processor, a MIPS® processor, a Power PC® processor, AMD® processor, or an ALPHA® processor. In addition, the controller 220 can be any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor, such as controller 220, can be a conventional microprocessor, but the controller 220 can also be any conventional processor, controller, microcontroller, or state machine. Controller 220 can also be implemented as a combination of computing devices, e.g., a combination of a DSP and a microprocessor, a plurality of microprocessors, one or more microprocessors in conjunction with a DSP core, or any other such configuration.

Data storage can refer to electronic circuitry that allows information, typically computer or digital data, to be stored and retrieved. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or one or more processors of the humidifier control system 106. Other types of memory include bubble memory and core memory. Data storage can be physical hardware configured to store information in a non-transitory medium.

Although certain preferred embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may be comprised of programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the above-described embodiments, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A surgical humidifier configured to respond to varying flow rates of a gas, the surgical humidifier comprising:
    a humidifier body;
    a chamber configured to removably engage with the humidifier body and hold a volume of water, the chamber comprising:
        an inlet port configured to receive a gas from an inlet conduit; and
        an outlet port configured to direct a humidified gas to a patient conduit;
    a chamber outlet temperature sensor configured to measure a temperature of the humidified gas;
    a flow sensor configured to measure a flow rate of the humidified gas;
    a heater plate coupled to the humidifier body and configured to deliver heat to the chamber; and
    a humidifier control system electrically coupled to the heater plate, the humidifier control system being configured to control an amount of electrical power delivered to the heater plate;
    wherein the humidifier control system is configured to receive a temperature measurement from the chamber outlet temperature sensor, to receive a flow rate reading from the flow sensor, to determine a control state of the humidifier control system selected from a plurality of predetermined control states based on the flow rate reading, to determine a chamber outlet temperature set point in response to the control state, and to adjust the amount of electrical power delivered to the heater plate based at least in part on a difference between the chamber outlet temperature set point and the temperature measurement, wherein the plurality of predetermined control states comprise one or more of a low flow state, a medium flow state, or a high flow state, wherein each of the plurality of predetermined control states corresponds to a range of flow rate readings and comprises an upper flow rate limit, or a lower flow rate limit, or both upper and lower flow rate limits,
    wherein the humidifier control system is further configured to:
        start a timer when the flow rate reading exceeds a threshold;
        switch to a second mode of use from a first mode of use when the flow rate reading exceeds the threshold for a defined duration; and
        provide the amount of electrical power to the heater plate in the surgical humidifier to achieve a chamber outlet temperature set point corresponding to the second mode of use.

2. The surgical humidifier of claim 1, wherein the humidifier control system comprises a control module configured to determine a mode of use based on at least one of a flow rate reading from the flow sensor or a temperature measurement from the chamber outlet temperature sensor.

3. The surgical humidifier of claim 1, wherein the humidifier control system comprises a chamber temperature feedback module configured to adjust the amount of electrical power delivered to the heater plate based at least in part on a difference between the chamber outlet temperature set point and the temperature measurement from the chamber outlet temperature sensor.

4. The surgical humidifier of claim 1, further comprising a heater plate temperature sensor configured to provide a measurement of a temperature of the heater plate.

5. The surgical humidifier of claim 4, wherein the humidifier control system comprises a control module configured to determine a mode of use based on at least one of the flow rate reading from the flow sensor, the temperature measurement from the chamber outlet temperature sensor, or the temperature measurement from the heater plate temperature sensor.

6. The surgical humidifier of claim 4, wherein the humidifier control system comprises a heater plate feedback module configured to adjust the amount of electrical power delivered to the heater plate based at least in part on a difference between a heater plate temperature set point and the temperature measurement from the heater plate temperature sensor.

7. The surgical humidifier of claim 1, wherein the low flow state has an upper flow rate limit of about 3 Liters per Minute (LPM).

8. The surgical humidifier of claim 1, wherein the medium flow state has an upper flow rate limit of about 5.5 Liters per Minute (LPM), and a lower flow rate limit of about 2 Liters per Minute (LPM).

9. The surgical humidifier of claim 1, wherein the high flow state has a lower flow rate limit of about 4.5 Liters per Minute (LPM).

10. The surgical humidifier of claim 1, wherein the chamber outlet temperature set point corresponding with the low flow state is about 37 degrees Celsius.

11. The surgical humidifier of claim 1, wherein the chamber outlet temperature set point corresponding with the medium flow state is about 35 degrees Celsius.

12. The surgical humidifier of claim 1, wherein the chamber outlet temperature set point corresponding with the high flow state is about 33 degrees Celsius.

13. The surgical humidifier of claim 1, wherein the humidifier control system is configured to switch to a first mode of use when the flow rate reading drops below the threshold.

14. The surgical humidifier of claim 1, wherein said low flow state has a higher chamber outlet temperature set point than the chamber outlet temperature set point of one or more of: the medium flow state, or the high flow state.

15. The surgical humidifier of claim 1, wherein the surgical humidifier is configured to move to a higher flow state when the flow rate reading exceeds the upper flow rate limit of a current control state.

16. The surgical humidifier of claim 1, wherein the surgical humidifier is configured to move to a lower control state when the flow rate reading drops below the lower flow rate limit of a current control state.

17. The surgical humidifier of claim 1, wherein the range of flow rates corresponding to the plurality of control state at least partially overlap.

18. The surgical humidifier of claim 1, wherein the low flow state consists of an upper flow rate limit.

19. The surgical humidifier of claim 1, wherein the medium flow state comprises an upper flow rate limit and a lower flow rate limit.

20. The surgical humidifier of claim 1, wherein the high flow state consists of a lower flow rate limit.

21. The surgical humidifier of claim 1, wherein the plurality of predetermined control states comprises the low flow state, the medium flow state, and the high flow state.

* * * * *

UNITED STATES PATENT AND TRADEMARK OFFICE
CERTIFICATE OF CORRECTION

PATENT NO. : 9,878,123 B2
APPLICATION NO. : 14/023391
DATED : January 30, 2018
INVENTOR(S) : Ali Ghalib Abdul Rahman Ghalib Page 1 of 1

It is certified that error appears in the above-identified patent and that said Letters Patent is hereby corrected as shown below:

In the Claims

In Column 22 at approximately Line 25, in Claim 17, change "state" to --states--.

Signed and Sealed this
Thirty-first Day of July, 2018

Andrei Iancu
*Director of the United States Patent and Trademark Office*